US012721592B2

(12) United States Patent
Krieger et al.

(10) Patent No.: US 12,721,592 B2
(45) Date of Patent: Sep. 1, 2026

(54) AUTONOMOUS ROBOTIC POINT OF CARE ULTRASOUND IMAGING

(71) Applicants: THE JOHNS HOPKINS UNIVERSITY, Baltimore, MD (US); UNIVERSITY OF MARYLAND, BALTIMORE, Baltimore, MD (US)

(72) Inventors: Axel Krieger, Alexandria, VA (US); Thorsten Roger Fleiter, Baltimore, MD (US); Lidia Al-Zogbi, Baltimore, MD (US)

(73) Assignees: THE JOHNS HOPKINS UNIVERSITY, Baltimore, MD (US); UNIVERSITY OF MARYLAND, BALTIMORE, Baltimore, MD (US)

(*) Notice: Subject to any disclaimer, the term of this patent is extended or adjusted under 35 U.S.C. 154(b) by 0 days.

(21) Appl. No.: 18/841,950

(22) PCT Filed: Feb. 28, 2023

(86) PCT No.: PCT/US2023/014008

§ 371 (c)(1),
(2) Date: Aug. 27, 2024

(87) PCT Pub. No.: WO2023/167830

PCT Pub. Date: Sep. 7, 2023

(65) Prior Publication Data

US 2025/0160787 A1 May 22, 2025

Related U.S. Application Data

(60) Provisional application No. 63/315,115, filed on Mar. 1, 2022.

(51) Int. Cl.
*A61B 8/00* (2006.01)
*A61B 8/08* (2006.01)

(52) U.S. Cl.
CPC .......... *A61B 8/4245* (2013.01); *A61B 8/0875* (2013.01); *A61B 8/4218* (2013.01); *A61B 8/5207* (2013.01)

(58) Field of Classification Search
None
See application file for complete search history.

(56) References Cited

U.S. PATENT DOCUMENTS 10,521,927 B2 12/2019 Teixeira et al.
2008/0200806 A1* 8/2008 Liu .......................... A61N 7/02
600/439

(Continued)

FOREIGN PATENT DOCUMENTS

CN 110477956 A 11/2019
CN 111916195 A 11/2020

(Continued)

OTHER PUBLICATIONS

CN-113855068-A machine translation (Year: 2021).*

(Continued)

*Primary Examiner* — Christopher Koharski
*Assistant Examiner* — Renee C Langhals
(74) *Attorney, Agent, or Firm* — MH2 Technology Law Group LLP

(57) ABSTRACT

A system for and method of autonomously robotically acquiring an ultrasound image of an organ within a bony obstruction of a patient is presented. The techniques include acquiring an electronic three-dimensional patient-specific representation of the bony obstruction of the patient; obtaining an electronic representation of a target location in or on the organ within the bony obstruction of the patient; determining, automatically, position and orientation of an ultrasound probe to acquire an image of the target location; and directing, autonomously, and by a robot, the ultrasound (Continued)

probe on the patient to acquire the image of the target location based on the position and orientation.

20 Claims, 10 Drawing Sheets

(56) References Cited

U.S. PATENT DOCUMENTS

| | | | | |
|---|---|---|---|---|
| 2020/0194117 | A1 | 6/2020 | Krieger et al. | |
| 2021/0236773 | A1 | 8/2021 | Dupont et al. | |
| 2022/0087654 | A1 * | 3/2022 | Mine | A61B 8/4245 |

FOREIGN PATENT DOCUMENTS

| | | | | |
|---|---|---|---|---|
| CN | 112151169 | A | 12/2020 | |
| CN | 112612274 | A | 4/2021 | |
| CN | 113288204 | A | 8/2021 | |
| CN | 113855068 | A * | 12/2021 | A61B 8/5215 |
| CN | 113858219 | A | 12/2021 | |

OTHER PUBLICATIONS

Wang, X. (Authorized officer), International Preliminary Report on Patentability in corresponding International Application No. PCT/US2023/014008 mailed on Sep. 12, 2024, 11 pages.

Matos, T. (Authorized officer), International Search Report and Written Opinion in corresponding International Application No. PCT/US2023/014008 mailed on May 23, 2023, 12 pages.

Abramowicz, Jacques S. et al. "World federation for ultrasound in medicine and biology position statement: how to perform a safe ultrasound examination and clean equipment in the context of COVID-19." Ultrasound in Medicine & Biology 46.7 (2020): 1821-1826.

Adams, Scott J. et al. "Telerobotic sonography for remote diagnostic imaging: narrative review of current developments and clinical applications." Journal of ultrasound in medicine 40.7 (2021): 1287-1306.

Baad, Michael et al. "Clinical significance of US artifacts." Radiographics 37.5 (2017): 1408-1423.

Blaivas, Michael. "Lung ultrasound in evaluation of pneumonia." Journal of Ultrasound in Medicine 31.6 (2012): 823-826.

Elsayad, Alaa M. "Completely unsupervised image segmentation using wavelet analysis and Gustafson-Kessel clustering." 2008 5th International Multi-Conference on Systems, Signals and Devices. IEEE, 2008.

He, Yisheng et al. "Pvn3d: a deep point-wise 3d keypoints voting network for 6dof pose estimation." Proceedings of the IEEE/CVF conference on computer vision and pattern recognition. 2020.

Huang, Gao et al. "Densely connected convolutional networks." Proceedings of the IEEE conference on computer vision and pattern recognition. 2017.

Ioffe, Sergey et al. "Batch normalization: Accelerating deep network training by reducing internal covariate shift." International conference on machine learning. pmlr, 2015.

Kim, Yeoun Jae et al. "Development of a control algorithm for the ultrasound scanning robot (NCCUSR) using ultrasound image and force feedback." The International Journal of Medical Robotics and Computer Assisted Surgery 13.2 (2017): e1756.

Kingma, Diederik P. "Adam: a method for stochastic optimization." arXiv preprint arXiv:1412.6980 (2014).

Lee, Ta-Chih et al. "Building skeleton models via 3-D medial surface axis thinning algorithms." CVGIP: graphical models and image processing 56.6 (1994): 462-478.

Liu, Xingyu et al. "Keypose: Multi-view 3d labeling and keypoint estimation for transparent objects." Proceedings of the IEEE/CVF conference on computer vision and pattern recognition. 2020.

Mathur, Bharat et al. "A semi-autonomous robotic system for remote trauma assessment." 2019 IEEE 19th International conference on bioinformatics and bioengineering (BIBE). IEEE, 2019.

Mathur, Bharat et al. "Evaluation of control strategies for a tele-manipulated robotic system for remote trauma assessment." 2019 Proceedings of the Conference on Control and its Applications. Society for Industrial and Applied Mathematics, 2019.

Mylonas, George P. et al. "Autonomous eFAST ultrasound scanning by a robotic manipulator using learning from demonstrations." 2013 IEEE/RSJ International Conference on Intelligent Robots and Systems. IEEE, 2013.

Narayana, P. A., et al. "The attenuation of ultrasound in biological fluids." The Journal of the Acoustical Society of America 76.1 (1984): 1-4.

Papazov, Chavdar et al. "Real-time 3D head pose and facial landmark estimation from depth images using triangular surface patch features." Proceedings of the IEEE conference on computer vision and pattern recognition. 2015.

Paszke, Adam et al. "Automatic differentiation in pytorch." (2017).

Peng, Qian-Yi et al. "Findings of lung ultrasonography of novel corona virus pneumonia during the 2019-2020 epidemic." Intensive care medicine 46 (2020): 849-850.

Pomerleau, François et al. "Comparing ICP variants on real-world data sets: Open-source library and experimental protocol." Autonomous robots 34 (2013): 133-148.

Quigley, Morgan et al. "ROS: an open-source Robot Operating System." ICRA workshop on open source software. vol. 3. No. 3.2. 2009.

Smith-Guerin, N. et al. "Clinical validation of a mobile patient-expert tele-echography system using ISDN lines." 4th International IEEE EMBS Special Topic Conference on Information Technology Applications in Biomedicine, 2003 . . IEEE, 2003.

Szalma, József et al. "The influence of the chosen in vitro bone simulation model on intraosseous temperatures and drilling times." Scientific Reports 9.1 (2019): 11817.

Teixeira, Brian et al. "Generating synthetic x-ray images of a person from the surface geometry." Proceedings of the IEEE conference on computer vision and pattern recognition. 2018.

Tsai, Roger Y. et al. "A new technique for fully autonomous and efficient 3 d robotics hand/eye calibration." IEEE Transactions on robotics and automation 5.3 (1989): 345-358.

Virga Salvatore et al. "Automatic force-compliant robotic ultrasound screening of abdominal aortic aneurysms." 2016 IEEE/RSJ international conference on intelligent robots and systems (IROS). IEEE, 2016.

Wang, Jing et al. "Application of a Robotic Tele-Echography System for COVID-19 Pneumonia." Journal of Ultrasound in Medicine 40.2 (2021): 385-390.

Wu, Shengzheng et al. "Robot-assisted teleultrasound assessment of cardiopulmonary function on a patient with confirmed COVID-19 in a cabin hospital." Advanced Ultrasound in Diagnosis and Therapy 4.2 (2020): 128-130.

Xu, Bing et al. "Empirical evaluation of rectified activations in convolutional network." arXiv preprint arXiv:1505.00853 (2015).

Yang, Geng et al. "Keep healthcare workers safe: application of teleoperated robot in isolation ward for COVID-19 prevention and control." Chinese Journal of Mechanical Engineering 33 (2020): 1-4.

Ye, Ruizhong et al. "Feasibility of a 5G-based robot-assisted remote ultrasound system for cardiopulmonary assessment of patients with coronavirus disease 2019." Chest 159.1 (2021): 270-281.

Zeiler, M. D. "ADADELTA: an Adaptive Learning Rate Method." arXiv preprint arXiv:1212.5701 (2012).

Al-Zogbi et al., "A 3-D Printed Patient-Specific Ultrasound Phantom for Fast Scan," Ultrasound in Med. & Biol., vol. 47, No. 3, pp. 820-832, 2021.

Buda et al., "Lung ultrasound in the diagnosis of COVID-19 infection—a case series and review of the literature," Advances in Medical Sciences 65 (2020) 378-385.

Etchison, "Letter to the Editor," Sports Health, Sep.-Oct. 2011, 1 page.

Laugier et al., "Chapter 2—Introduction to the Physics of Ultrasound," ResearchGate, Nov. 2010, 18 pages.

* cited by examiner 606
604
602
600

700

AUTONOMOUS ROBOTIC POINT OF CARE ULTRASOUND IMAGING

CROSS-REFERENCE TO RELATED APPLICATIONS

This application is the national stage entry of International Patent Application No. PCT/US2023/014008, filed on Feb. 28, 2023, and published as WO 2023/167830 A1 on Sep. 7, 2023, which claims the benefit of U.S. Provisional Patent Application No. 63/315,115, filed on Mar. 1, 2022, which are hereby incorporated by reference herein in their entireties.

FIELD

This disclosure relates generally to ultrasound imaging.

BACKGROUND

The COVID-19 pandemic has emerged as a serious global health crisis, with the primary morbidity and mortality linked to pulmonary involvement. A prompt and accurate diagnostic assessment is thus crucial for understanding and controlling the spread of the disease, with point of care ultrasound scanning ("POCUS") becoming one of the primary determinative methods for its diagnosis and staging. Although safer and more efficient than other imaging modalities, POCUS requires close contact of radiologists and ultrasound technicians with patients, subsequently increasing the risk for infections.

Tele-operated solutions allow medical experts to remotely control the positioning of an ultrasound probe attached to a robotic system, thus reducing the distance between medical personnel and patients to a safer margin. Several tele-operated systems have been successfully tested amidst the pandemic for various purposes. While they are a better alternative to traditional in-person POCUS, existing tele-operated systems nonetheless involve the presence of at least one healthcare worker in close vicinity of the patient to initialize the setup and assist the remote sonographer. Further, tele-operated systems require a skilled sonographer to remotely control the ultrasound probe, and such experienced technicians are in high demand during the pandemic.

SUMMARY

According to various embodiments, a method of autonomously robotically acquiring an ultrasound image of an organ within a bony obstruction of a patient is presented. The method includes: acquiring an electronic three-dimensional patient-specific representation of the bony obstruction of the patient; obtaining an electronic representation of a target location in or on the organ within the bony obstruction of the patient; determining, automatically, position and orientation of an ultrasound probe to acquire an image of the target location; and directing, autonomously, and by a robot, the ultrasound probe on the patient to acquire the image of the target location based on the position and orientation.

Various optional features of the above method include the following. The method may include outputting the image of the target location. The bony obstruction may include a ribcage, and the organ may include at least one of: a lung, a heart, a spleen, a liver, a pancreas, or a kidney. The acquiring may include acquiring a three-dimensional radiological scan of the patient. The acquiring may include acquiring a machine learning representation of the bony obstruction of the patient based on a topographical image of the patient. The obtaining may include obtaining a human specified location in the electronic three-dimensional representation of the bony obstruction of the patient. The method may include: measuring a force on the ultrasound probe; and determining a position of the ultrasound probe, based on the force, relative to the bony obstruction of the patient. The determining may include determining position and orientation based on a weighted function of a plurality of material densities, and the plurality of material densities may include a bone density. The organ may include a lung, and the plurality of material densities may further include a density of air. An image of the target location may be acquired without requiring proximity of a technician to the patient.

According to various embodiments, a system for autonomously robotically acquiring an ultrasound image of an organ within a bony obstruction of a patient is presented. The system includes: an electronic processor that executes instructions to perform operations including: acquiring an electronic three-dimensional patient-specific representation of the bony obstruction of the patient, obtaining an electronic representation of a target location in or on the organ within the bony obstruction of the patient, and determining, automatically, position and orientation of an ultrasound probe to acquire an image of the target location; and a robot communicatively coupled to the electronic processor, the robot comprising an effector couplable to an ultrasound probe, the robot configured to direct the ultrasound probe on the patient to acquire the image of the target location based on the position and orientation.

Various optional features of the above system include the following. The operations may further include outputting the image of the target location. The bony obstruction may include a ribcage, and the organ may include at least one of: a lung, a heart, a spleen, a liver, a pancreas, or a kidney. The acquiring may include acquiring a three-dimensional radiological scan of the patient. The acquiring may include acquiring a machine learning representation of the bony obstruction of the patient based on a topographical image of the patient. The obtaining may include obtaining a human specified location in the electronic three-dimensional representation of the bony obstruction of the patient. The operations may further include: measuring a force on the ultrasound probe; and determining a position of the ultrasound probe, based on the force, relative to the bony obstruction of the patient. The determining may include determining position and orientation based on a weighted function of a plurality of material densities, and wherein the plurality of material densities may include a bone density. The organ may include a lung, and the plurality of material densities may further include a density of air. The robot may be configured to acquire an image of the target location without requiring proximity of a technician to the patient.

DRAWINGS

The above and/or other aspects and advantages will become more apparent and more readily appreciated from the following detailed description of examples, taken in conjunction with the accompanying drawings, in which.

DETAILED DESCRIPTION

Figure 1:
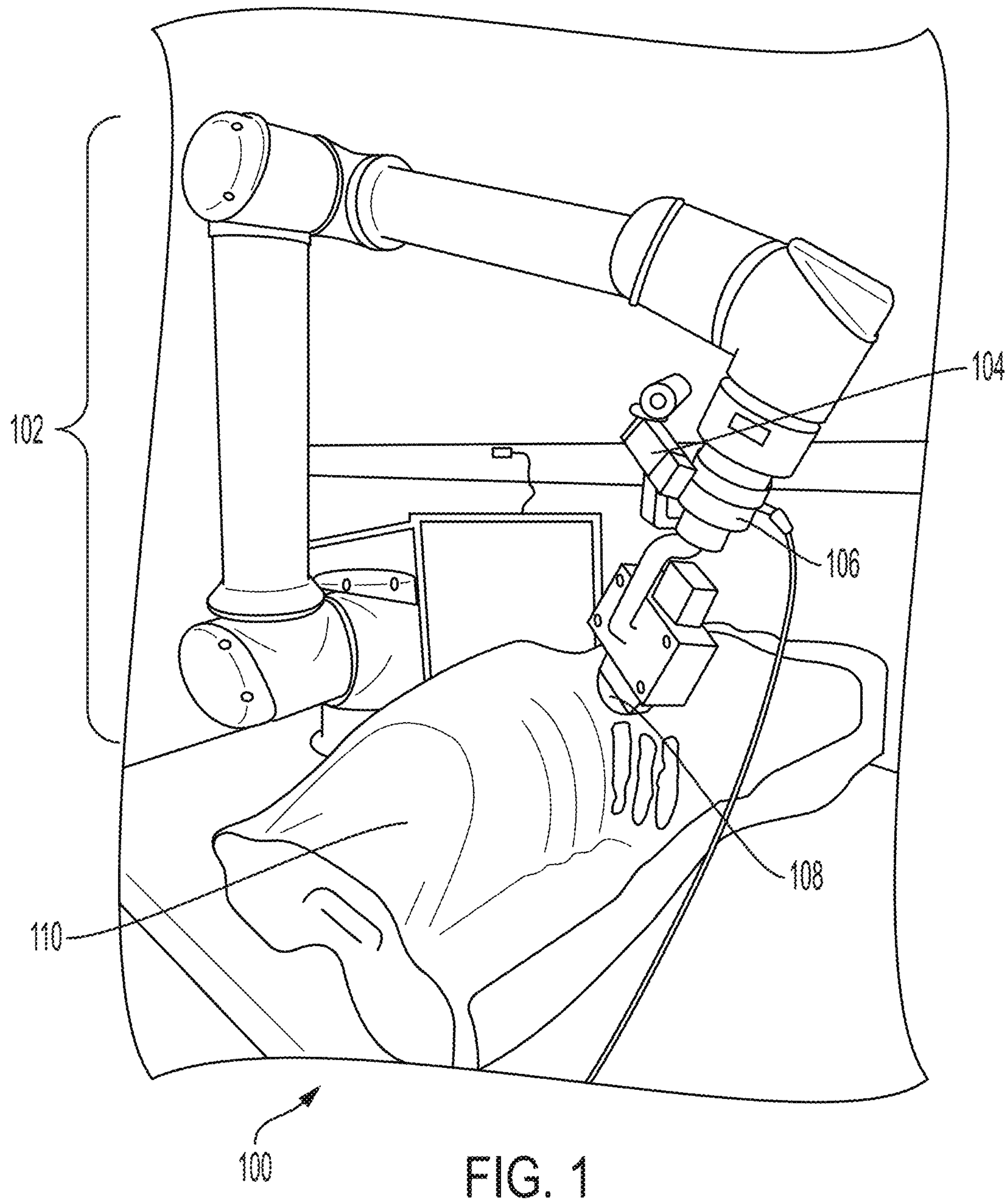
FIG. 1 depicts hardware elements of an autonomous robotic ultrasound imaging system according to various embodiments.

Embodiments as described herein are described in sufficient detail to enable those skilled in the art to practice the invention and it is to be understood that other embodiments may be utilized and that changes may be made without departing from the scope of the invention. The present description is, therefore, merely exemplary.

I. Introduction

The COVID-19 pandemic has emerged as a serious global health crisis, with the predominant morbidity and mortality linked to pulmonary involvement. Point of care ultrasound (POCUS) scanning, becoming one of the primary determinative methods for its diagnosis and staging, requires, however, close contact of healthcare workers with patients, therefore increasing risk of infection.

While tele-operated solutions, which allow medical experts to remotely control the positioning of an ultrasound probe attached to a robotic system, reduce the distance between medical personnel and patients to a safer margin, existing tele-operated ultrasound systems nonetheless require both a skilled remote sonographer and the presence of at least one healthcare worker in close vicinity of the patient to initialize the setup and assist the sonographer.

An autonomous robotic ultrasound system would better limit physical interaction between healthcare workers and infected patients, while offering more accuracy and repeatability to enhance imaging results, and hence patient outcomes. Further, an autonomous system would be a valuable tool for assisting less experienced health care workers, especially amidst the COVID-19 pandemic where trained medical personnel is such a scarce resource. However, existing autonomous ultrasound systems are insufficient for COVID-19 POCUS applications, which involve ultrasound imaging of the patient's lungs.

In general, robotic POCUS of lungs faces several difficulties, including: (a) the large volume of the organ, which cannot be inspected in a single ultrasound scan, implying that during each session, multiple scans from different locations may be sequentially collected for monitoring the disease's progression, (b) the scattering of ultrasound rays through lung air, meaning that an autonomous solution may be patient-specific to account for different lung shapes and sizes to minimize this effect, and (c) the potential obstruction of the lungs by the ribcage, which would result in an uninterpretable scan due to the impenetrability of bone material by ultrasound waves.

Embodiments disclosed herein solve one or more of the above problems. Some embodiments provide autonomous robotic POCUS ultrasound scanning of lungs, e.g., for COVID-19 patient diagnosis, monitoring, and staging.

Some embodiments robotically and autonomously position an ultrasound probe based on a patient's prior CT scan to reach predefined lung infiltrates. Some embodiments provide lung ultrasound scans using force feedback on the robotically controlled ultrasound probe based on a patient's prior CT scan.

Some embodiments predict anatomical features of a patient's ribcage using a surface torso model. Some embodiments utilize a deep learning technique for predicting 3D landmark positions of a human ribcage given a torso surface model. According to such embodiments, the landmarks, combined with the surface model, may be used for estimating ultrasound probe position on the patient for robotically and autonomously imaging infiltrates.

An experimental embodiments, described throughout this disclosure, acquired ultrasound scans with an average accuracy of 20.6±14.7 mm based prior CT scans, and 19.8±16.9 mm based on only ribcage landmark estimation using a surface model. A study of the experimental embodiment used on a full torso ultrasound phantom showed that the autonomously acquired ultrasound images were 100% interpretable when using force feedback with a prior CT and 87.5% with landmark estimation, compared to 75% and 58.3% without force feedback, respectively. This demonstrates the potential for embodiments to acquire accurate POCUS scans while mitigating the spread of COVID-19 in vulnerable environments.

II. Overview

FIG. 1 depicts hardware elements of an autonomous robotic ultrasound imaging system 100 according to various embodiments. System 100 as shown includes robot effector 102, depth camera 104, force/torque sensor 106, and ultrasound probe 108. An experimental embodiment, as shown in FIG. 1, included six degrees of freedom UR10e robot (Universal Robot, Odense, Denmark) for the effector 104, a world frame color camera Intel RealSense D415 (Intel, Santa Clara, California, USA) for the depth camera 106, an SI-65-5 six-axis F/T Gamma transducer (ATI Industrial, Apex, North Carolina, USA) for the force/torque sensor 106, and a C3 wireless ultrasound probe (Clarius, Burnaby, British Columbia, Canada) for the ultrasound probe 108. By way of non-limiting example, as shown n FIG. 1, the ultrasound probe 108 and depth camera 104 may be attached to the robot's end effector 102 in series with the force/torque sensor 106 for measuring the forces experienced along the tip of the ultrasound probe 108. In the experimental embodiment, the depth camera 104 was positioned behind the ultrasound probe 108 to visualize it in the camera frame, as well as the scene in front of it. Further in the experimental embodiment, an M15 Alienware laptop (Dell, Round Rock, Texas, USA) with a single 6 GB NVIDIA GeForce GTX 1660 Ti GPU memory card was used for controlling the robot. In general, any suitable computer may be used to control the robot according to various embodiments.

As shown in FIG. 1, for validation of the experimental embodiment, a custom-made full torso patient-specific ultrasound phantom 110 was used to provide a realistic model of a patient's torso. The geometry of phantom 110 and its simulated organs were obtained from the CT scan of a 32 year-old anonymized male patient with low body mass index (BMI). The tissues were made of a combination of two different ballistic gelatin materials to achieve human-like stiffness, cast into 3D printed molds derived from the CT scan. The skeleton was 3D printed in polycarbonate, and the mechanical and acoustic properties of the phantom 110 were evaluated, showing great similitude to human tissue properties. An expert radiologist positively reviewed the phantom 110 under ultrasound imaging.

Figure 2:
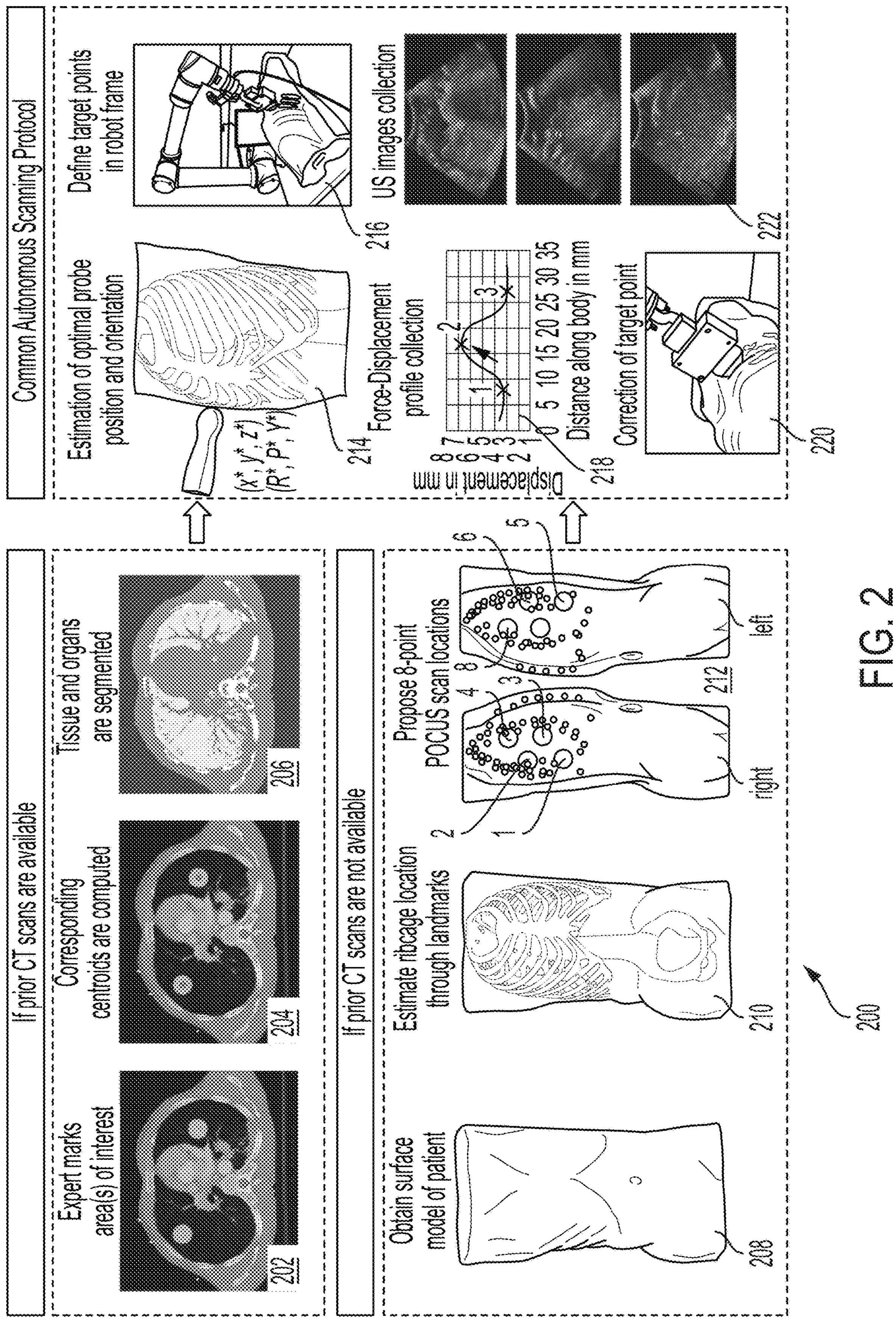
FIG. 2 is a workflow diagram for an autonomous robotic ultrasound imaging method according to various embodiments.

FIG. 2 is a workflow diagram 200 for an autonomous robotic ultrasound imaging method according to various embodiments. The method depicted in FIG. 2 may be implemented using, for example, system 100 as shown and described above in reference to FIG. 1. As shown in FIG. 2, the autonomous robotic ultrasound imaging method may be implemented with or without use of a prior patient CT scan. An overview of both techniques is presented below, and individual features and elements are described in detail herein in reference to FIGS. 3-10.

If a prior patient chest CT scan is available, then at 202 an expert radiologist or other medical technician marks on the CT regions of interest (typically but not necessarily containing infiltrates), which may then be observed over the course of coming days to evaluate the progression of the disease. The technician may be situated anywhere in the world relative to the patient and need not be present with the patient, or even in the same room or building, at the time of the ultrasound scan. At 204, an algorithm computes the spatial centroid of each region, as shown and described in detail in reference to FIG. 8. Based on segmentations generated per 206, at 214 the system determines positions and orientations of an ultrasound probe on a subject's body, such that the resultant ultrasound image will contain the specified point of interest without skeletal obstruction.

If a CT scan is not available, landmarks of the ribcage are estimated using the patient's 3D mesh model, which is generated at 208 from a topographical image of the patient obtained using a depth camera, e.g., depth camera 104. At 210, the location of the patient's ribcage is estimated by mapping landmarks. In the experimental embodiment, a neural network deep learning algorithm was used to estimate the ribcage landmarks from the 3D mesh model. Scanning points are then manually selected at 212 on the model following the 8-point POCUS protocol, e.g., by an expert radiologist or other medical technician. As with the CT scan technique, the technician may be situated anywhere in the world relative to the patient and need not be present with the patient, or even in the same room or building, at the time of the ultrasound scan. Goal positions and orientations are then determined at 214.

Note that in some embodiments, the method may utilize both a CT scan and a surface model as described above to generate probe positions and orientations at 214.

Whether a CT scan is used, a mesh model is used, or both, the probe positions and orientations of 214 are converted to robotic control signals for the robot frame at 216. Further description of such conversion is shown and disclosed herein in reference to FIG. 5.

Due to possible kinematic and registration errors, the positioning of the ultrasound probe may suffer from unknown displacements, which can compromise the quality and thus interpretability of the ultrasound scans. To mitigate this, some embodiments employ a force-feedback mechanism through the ultrasound probe, e.g., using force/torque sensor 106, to avoid skeletal structures that will lead to shadowing. In more detail, a force-displacement profile is collected at 218, which is used to correct the end effector's position at 220 to avoid imaging of bones. The specifics of this protocol are further shown and described in detail herein, e.g., in reference to FIG. 4.

Finally, the robot collects the ultrasound images at 222. For example, the robot executes the robotic control signals to achieve the ultrasound positions and orientations of an ultrasound probe relative to the patient to acquire images of the target location.

In the experimental embodiment, the ultrasound scanning position and orientation algorithm of 214, as well as the ribcage landmarks estimation of 210, were implemented in Python, whereas the robot control, which includes planning and data processing algorithms, were integrated via Robot Operating System as disclosed in Quigley, M., Conley, K., Gerkey, B., Faust, J., Foote, T., Leibs, J., et al. (2009), ROS: *An open-source robot operating system*, ICRA workshop on open source software (Kobe, Japan), vol. 3.2, 5. Kinematics and Dynamics Library (KDL) in Open Robot Control Systems (OROCOS) was used to transform the task-space trajectories of 214 of the robot to the joint space trajectories of 216, which are output by the high-level autonomous control system. The drivers developed by Universal Robot allow to apply the low-level controllers to the robot to follow the desired joint-space trajectories.

III. Ultrasound Position and Orientation From CT Scan

Details of techniques for determining ultrasound probe scanning position and orientation based on a CT scan are presented in this section.

Figure 3:
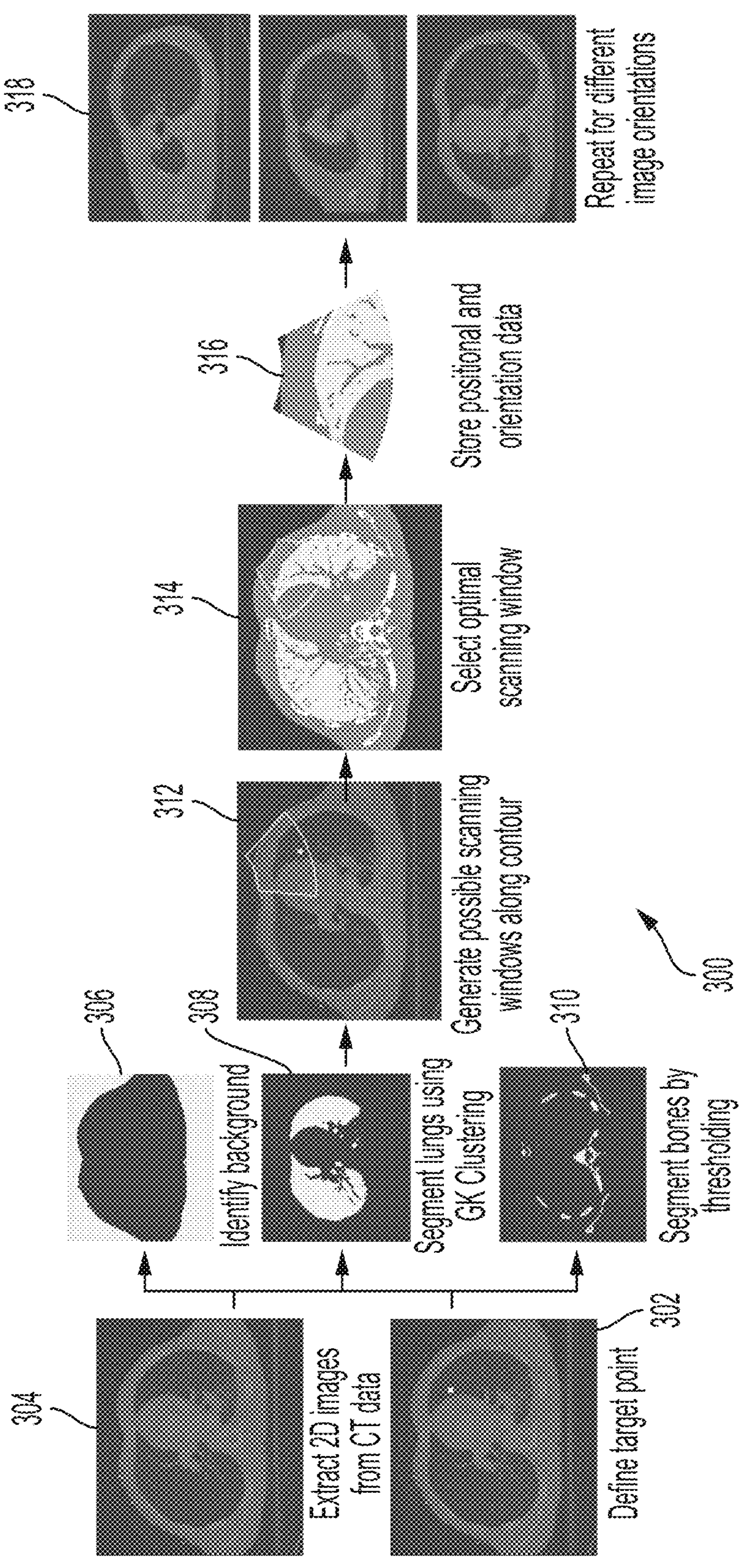
FIG. 3 is a workflow diagram of a technique for selecting scanning target locations according to various embodiments.

FIG. 3 is a workflow diagram 300 of a technique for selecting scanning target locations according to various embodiments. A prior CT scan of a patient's chest is obtained and used as an input to the algorithm disclosed presently. By way of non-limiting example, the possible scanning area on the body of a given patient is limited to the frontal and side regions. Given a region of interest in the lungs specified by a medical expert or other technician, at 302 its spatial centroid is computed at first to define a target point. The procedure thus initially targets imaging a single point, followed by a sweeping motion about the contact line of the ultrasound probe to encompass the surrounding area. At 304, a set of images from the CT data containing the computed centroid is generated at various orientations, each of which is subsequently segmented into four major classes: (a) soft tissues, (b) lung air, (c) bones, and (d) background. At 306, the background is identified using a combination of thresholding, morphological transformations, and spatial context information. The inverse of the resultant binary mask thus delimits the patient's anatomy from the background. At 308, the inverse mask is then used to restrict the region in which lung air is identified and segmented through Gustafson-Kessel clustering, e.g., as disclosed in Elsayad, A. M. (2008), *Completely unsupervised image segmentation using wavelet analysis and Gustafson Kessel clustering,* 2008 5th International Multi-Conference on Systems, Signals and Devices (IEEE), 495 1-6. At 310, the bones are segmented using an intensity thresholding cutoff of 1250, combined with spatial context information. Soft tissues are lastly identified by subtracting the bones and lung air masks from the inverse of the background mask. For simplicity's sake, and byway of non-limiting example, identical acoustic properties may be considered for all soft tissues within the patient's body. This assumption is justified by comparing the acoustic properties of various organs in the lungs' vicinity (e.g., soft tissue, liver, spleen), which were shown to be sufficiently close to each other in the experimental embodiment.

The objective is to image the pre-determined target points within the lungs, while maximizing the quality of the ultrasound scan, which is influenced by three major factors; (a) proximity of the target to the ultrasound probe, (b) medium through which the ultrasound beam travels, and (c) number of layers with different acoustic properties the beam travels across. The quality of an ultrasound scan is enhanced as the target is closer to the ultrasound probe. In the particular case of lung scanning, directing beams through air should be avoided due to the scattering phenomenon, which significantly reduces the interpretability of the resulting scan. Skeletal structures reflect ultrasound almost entirely, prompting the user to avoid them. Lastly, layers of medium with different attenuation coefficients induce additional refraction and reflection of the signal, negatively impacting the imaging outcomes.

The problem can be formulated as a discrete optimization solved by linear search, whereby the objective is to minimize the sum of weights assigned to various structures in the human body through which the ultrasound beam travels, along with interaction terms modeling refraction, reflection and attenuation of the signal. Let $\vec{p}_i \in \mathbb{R}^2$ represent the 2D coordinates of a pixel i inside the ultrasound beam cone (see 312 and 314 for cone reference). Let $\vec{p}_{f_c} \in \mathbb{R}^2$ represent the pixel corresponding to the focal point of the ultrasound probe, that is, the point of origin of the ultrasound signal. Note that this pixel may be a virtual pixel that is not imaged. The attenuation of the ultrasound signal may be evaluated through the following equation:

$$w_{i,c} = w_{0,c}\left[\exp\left(-\alpha\Delta\|\vec{p}_i - \vec{p}_{f_c}\|_2\right)\right]^{-1} \quad (1)$$

In Equation (1), $w_{i,c}$ represents the weight of the first pixel pertaining to the same class c, $\alpha$ represents the attenuation coefficient of the medium, and $\Delta$ represents the spatial resolution of the CT scan. To model the intensity reflection of the ultrasound beam at the interface of two different mediums, first the intensity reflection coefficient $\gamma$ is evaluated, and subsequently applied to the weight of the first pixel following the interface boundary:

$$\gamma = \frac{(\rho_2 v_2 - \rho_1 v_1)^2}{(\rho_2 v_2 + \rho_1 v_1)^2} \quad (2)$$

$$w^*_{i,c} = w_{i,c}(\gamma)^{-1} \quad (3)$$

In Equations (2) and (3), $\rho$ represents tissue density, and $v$ represents the speed of ultrasound. The term $\rho v$ effectively represents the impedance of the medium, with medium 1 preceding medium 2. The algorithm thus evaluates the weight of every pixel in between the first point of contact of the ultrasound probe and the target point, with higher weights assigned to more attenuated pixels, as they would drastically reduce the image quality. At 314, the ultrasound path that results in the lowest weight, from among multiple paths generated at 312 whose respective cones include the target location, is selected, e.g., as the optimal one.

To this end, bones were assigned the highest weight of 109, since ultrasound rays cannot travel past them. The second highest weight was assigned to lung air at 5, followed by soft tissues at 1. These example weights are non-limiting. The assumed attenuation coefficients for skeletal tissue, lung air, and soft tissues are 1.1 dB/(mm×MHz), 1.2 dB/(mm×MHz) and 0.12 dB/(mm×MHz) respectively. The assumed densities of each class are 2000 kg/$m^3$, 1.225 kg/$m^3$ and 1000 kg/$m^3$, whereas the speed of sound is 3720 m/s, 330 m/s, and 1575 m/s, respectively.

At 312, for a single image of the images of various orientations generated at 304, multiple possible scanning windows are generated, each containing the target point. The weights are computed within an ultrasound cone that can only be instantiated from the surface of the patient's body across all generated images. The algorithm first determines the scanning position and orientation, e.g., an optimal scanning position and orientation, of the probe for each individual image at 314, and finally selects the image with the overall lowest returned weight after 318. For each image, the position of the ultrasound cone, as well as the orientation of the image, define the selected, e.g., optimal, ultrasound scanning position and orientation in the CT coordinate frame, which is stored at 316. Finally, at 318, the process is repeated for each of the multiple images of various orientations obtained at 304. In the experimental embodiment, the solution was deployed on the Alienware laptop used for the robot control. Pseudocode for the ultrasound probe scanning position and orientation algorithm is presented below.

---

Algorithm: Ultrasound Probe Scanning Position and Orientation
input: CT scan, target point $\vec{p}_t \in \mathbb{R}^3$, angle resolution $\Delta\beta = 5$, $\Delta$ in mm
procedure
  extract $N \times M$ image $I_0$ from CT in axial plane s.t. $\vec{p}_t \in I_0$
  extract $N' \times M'$ images $I_i$ from CT in tilted planes at angles $\Delta\beta$ s.t. $\vec{p}t \in I_i$
  generate background masks $M_{BK,i}$ for $I_i$, i: $0 \to k$
  generate lung air masks $M_{L,i}$ for $I_i$, i: $0 \to k$
  generate bone masks $M_{BN,i}$ for $I_i$, i: $0 \to k$
  generate soft tissue masks $M_{T,i}$ for $I_i$, i: $0 \to k$
  replace $I_i$ with $M_i := M_{BK,i} + M_{T,i} + M_{L,i} + M_{BN,i}$, i: $0 \to k$
  initialize empty weight vector $W \in \mathbb{R}^{(k+1)\times L}$
  For i := 0 to k do
    generate L ultrasound beam contours C for $I_i$ s.t. $\vec{p}_t \in A_l$, $A_l$ := area enclosed by contour
    For j := 0 to L − 1 do
      define $\vec{d} = \vec{p}_t - \vec{p}_{fc}$
      define $\vec{p}_{closest} := \text{argmin}\ (\|\vec{p}_{US} - \vec{p}_{fc}\|_2)$ s.t. $\vec{p}_{US} \in \vec{d}$
      reinitialize $\vec{d} := \vec{p}_{closest} - \vec{p}_t$
      define vector $\vec{p}_t := [M_i[\vec{p}_{closest}], \ldots, M_i[\vec{p}_t]]^T$ that contain all pixels values along $\vec{d}$
      initialize $w = \vec{p}[0]$
      initialize $w_{0,T} = 1$, $W_{0,L} = 1$, and $w_{0,b} = 10^9$
      For t := 1 to length($\vec{p}$) do
        If $\vec{p}[t-1] \neq \vec{p}[t]$ do $$\vec{p}\left[t\text{: end} = \vec{p}[t\text{: end}]\left[\frac{(\rho_t v_t - \rho_{t-1} v_{t-1})^2}{(\rho_t v_t + \rho_{t-1} v_{t-1})^2}\right]^{-1}\right.$$

update $w_{0,c}$ according to $\vec{p}$[t: end] for corresponding classes
        $w = w + w_{0,c}[\exp(-\alpha_c\Delta\|\vec{p}_i - \vec{p}_{closest}\|_2)]^{-1}$
    append w to W
  return by linear search $w_{min} := \text{argmin}(W)$
  return $\vec{p}_{goal} \in \mathbb{R}^3$ corresponding to $w_{min}$ evaluated from plane transformation
  return $R_{goal} \in SO(3)$ corresponding to $w_{min}$ evaluation from plane transformation
output: $\vec{p}_{goal}$, $R_{goal}$, and $w_{min}$ For the output of the ultrasound probe scanning position and orientation algorithm, $\vec{p}_{goal}$ represents the position of the ultrasound probe, $R_{goal}$ represents the orientation of the ultrasound probe, and $w_{min}$ represents the minimum weight that is returned, indicating the optimality of $\vec{p}_{goal}$ and $R_{goal}$.

---

IV. Force-Displacement Profiles Along the Ribcage

Uncertainties in patient registration and robot kinematics can result in a partial or complete occlusion of the region of interest due to the misplacement of the ultrasound probe. To mitigate this problem, some embodiments utilize a force-feedback mechanism. According to some embodiments, for a constant force application of, by way of non-limiting example, 20 N, which is the recommended value for abdominal ultrasound imaging, the probe's displacement is higher in-between the ribs as opposed to being on the ribs. Force feedback can thus be used to generate a displacement profile across the ribcage of a patient to detect regions obstructed by ribs. The displacement generally follows a sinusoidal profile, with peaks (i.e., largest displacements) corresponding to a region in-between the ribs, and troughs (i.e., smallest displacement) corresponding to a region on the ribs.

Figure 4:
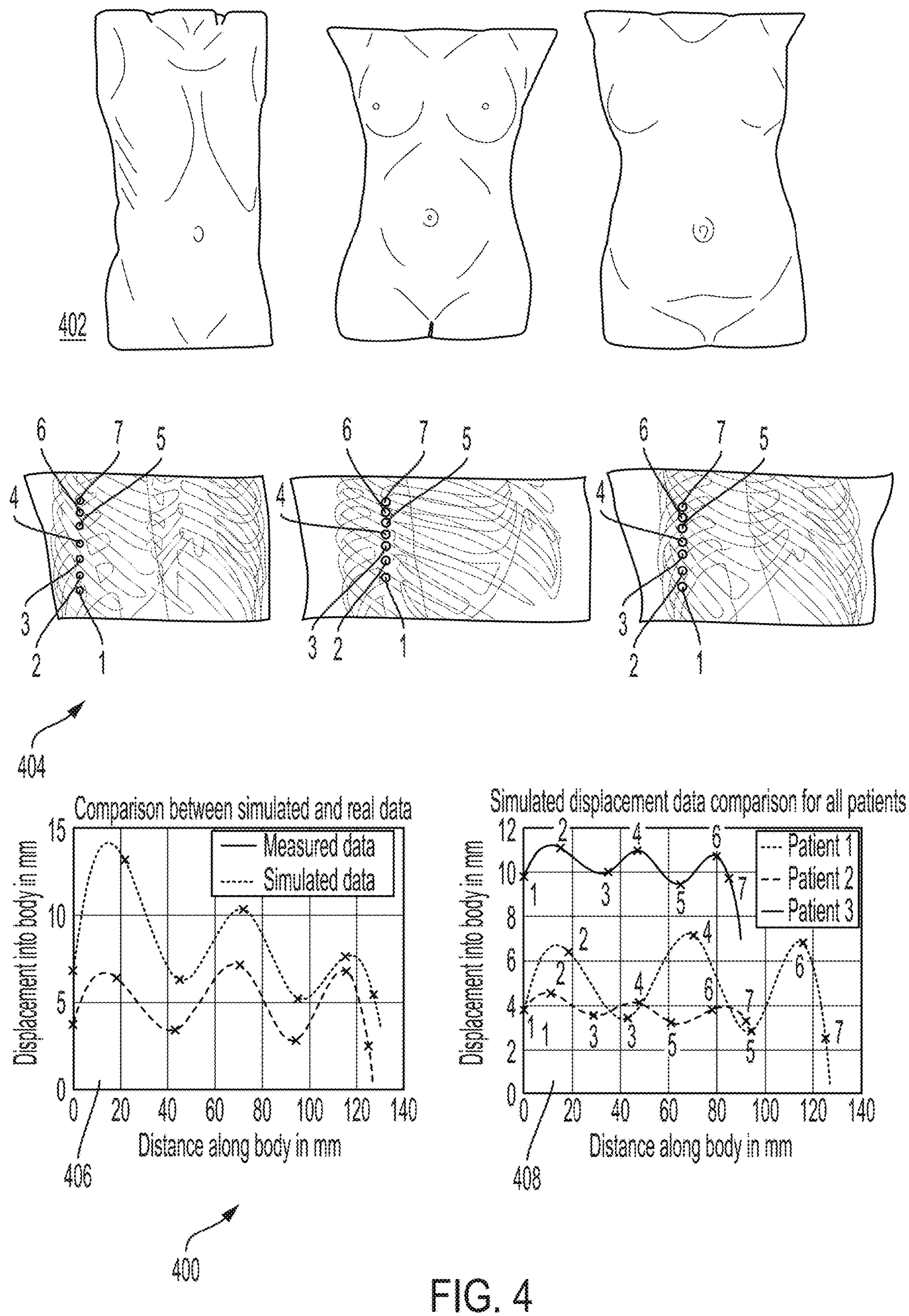
FIG. 4 depicts elements of force-displacement validation experiments used to validate the force feedback mechanism according to some embodiments.

FIG. 4 depicts elements 400 of force-displacement validation experiments used to validate the force feedback mechanism according to some embodiments. Experiments were conducted using computer simulations on both virtual models and on the physical phantom described herein.

In particular, the force feedback mechanism was validated based on computer-generated solid models 402 of n=3 virtual patient torsos using anonymized CT scans, which were used to simulate displacements using finite element analysis (FEA) in ANSYS (ANSYS, Canonsburg, Philadelphia, USA). Two of the patients were female. The third patient was male, and was used as the model for the phantom's creation. All patients used for the solid models had varying BMI. The different organs of the patients were extracted from the CT scans using Materialize Mimics (Materialize NV, Southport, QLD 4222, Australia) software as STL files, and subsequently converted through SOLIDWORKS (SolidWorks Corp., Dassault Systemes, Velizy-Villacoublay, France) into IGS format, thus transforming the mesh surfaces into solid models that can undergo material assignment and FEA simulations. The tissues" mechanical properties for the female patients were obtained from the literature, whereas those of the phantom were measured experimentally. In the FEA simulations, the force was transmitted onto the bodies through a CAD model of the ultrasound probe. In the robotic implementation, the ultrasound probe did not slip on a patient's body when contact was established because of the setup's rigidity. A lateral displacement of the probe in simulation would be erroneously translated into soft tissue displacement since the probe's tip displacement was used to represent the soft tissue displacement. Thus, to ensure that the motion of the probe is confined to a fixed vector, the virtual probe's motion was locked in all directions except in the z-axis. The virtual force was directly applied to the virtual probe through a force load that gradually increases from 0 to 20 N over a period of five seconds. The virtual probe was initially positioned at a very close proximity from the torso, hence its total displacement was considered to be a measure of the tissue's displacement. The simulations were deployed on a Dell Precision workstation 3620 with an 7 processor and 16 GB of RAM. Each displacement data point required on average 2.5 hours to converge. The location of the collected data points, as well as returned displacement profile for all three virtual patients are shown at 408 of FIG. 4. Cubic splines were used to fit the data to better visualize the trend using MATLAB's curve fitting toolbox. Cubic splines were considered for better visualizing the profiles, assuming a continuous and differentiable function to connect data points. The actual displacements in between the minimum and maximum, however, may not match the displayed spline.

To verify the outcome of the simulations, corresponding displacement profiles were collected from the physical phantom, which are shown at 406 of FIG. 4. Although the physical test demonstrated overall larger displacements, the physical displacement trend was similar to those of the simulated experiments. The results thus validate that varying displacements are associated with different positioning of an ultrasound probe with respect to the ribs.

Thus, some embodiments include a force-feedback mechanism in the robot's control process, whereby the system collects several displacement data points around the goal position at 20 N, to ensure that the ultrasound image is obtained in-between the ribs.

V. Ribcage Landmark Prediction

Some embodiments use 3D landmarks defined on the ribcage to estimate the appropriate, e.g., optimal, probe position. Some embodiments use a deep convolutional neural network trained to estimate the 3D position of 60 landmarks on the ribcage from the skin surface data. The trained 3D deep convolutional network directly estimated the landmark coordinates in 3D from the 3D volumetric mask representing the skin surface of a patient's torso.

In the experimental embodiment, the landmarks were defined using the segmentation masks of ribs obtained from the CT data. From the segmentation masks, the 3D medial axis for each rib was computed using a skeletonization algorithm. The extremities and center of each rib for the first 10 rib pairs (T1 to T10) were used as landmark locations. The three landmarks thus represent the rib-spine intersection, the center of the rib and the rib-cartilage intersection.

For training the deep neural network of the experimental embodiment, given the skin mask, a 3D bounding box covering the thorax region was estimated, using jugular notch on top and pelvis on the bottom. This region was then cropped and resized to 128×128×128 volume, which was used as input to a deep network. The network output a 3×60 matrix, which represents the 3D coordinates of the 60 rib landmarks. The experimental embodiment used the DenseNet architecture with batch normalization, and LeakyReLU activations with a slope of 0.01 following the 3D convolutional layers with kernel size of 5×5. The network parameters were optimized using AdaDelta.

VI. Control Strategy for Skeletal Structure Avoidance

Figure 5:
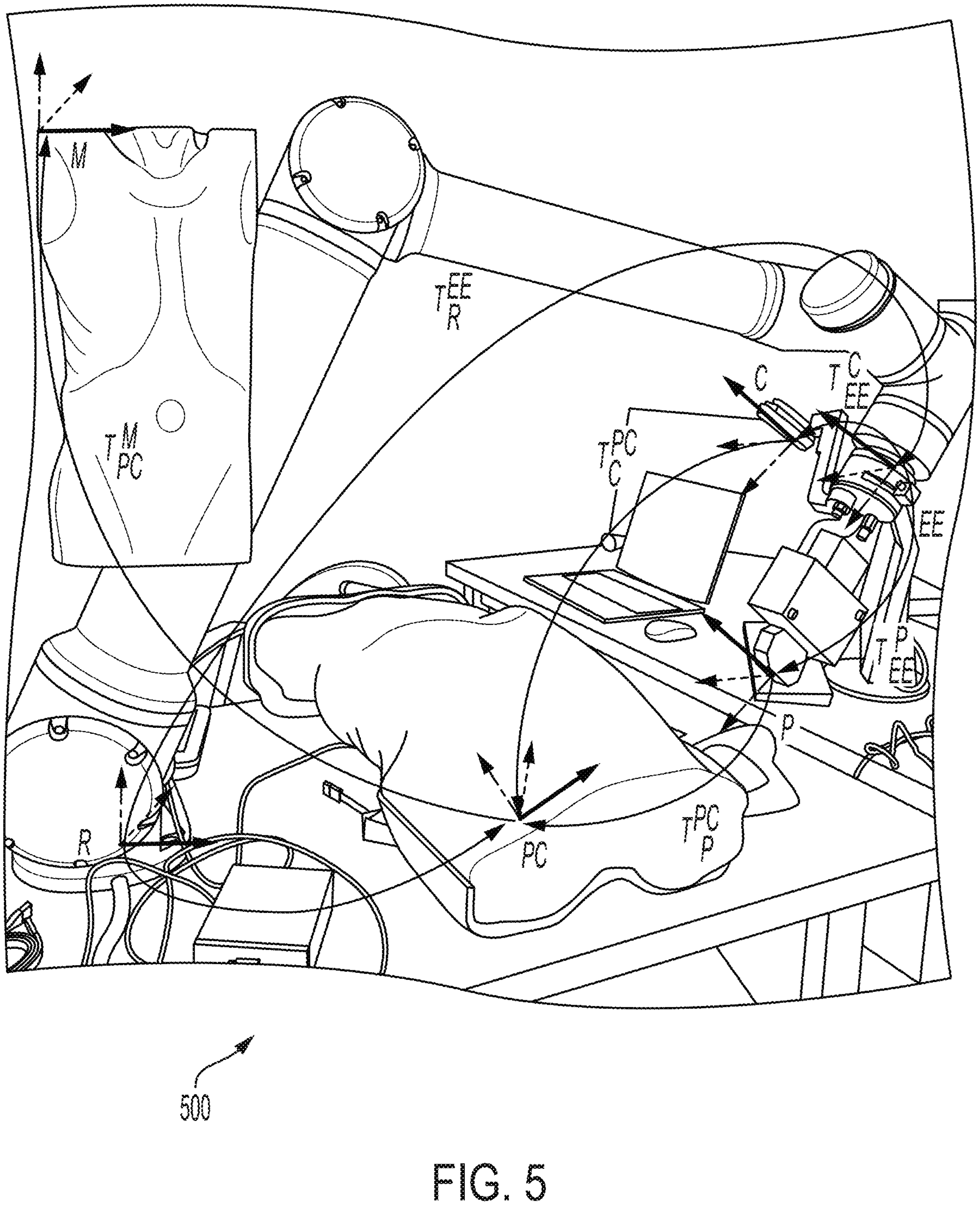
FIG. 5 depicts reference frames of a robotic manipulator along with transitions between them according to various embodiments.

The autonomous positioning of the ultrasound probe in contact with the patient's body utilizes motion and control planning, a non-limiting example of which is described presently in reference to FIG. 5.

FIG. 5 depicts reference frames and transitions 500 of a robotic manipulator according to various embodiments. The reference frames and transitions between them 500 as depicted in FIG. 5 were utilized in the experimental embodiment described throughout herein.

For notation, let $$T_B^A$$

denote the homogeneous transformation matrix from frames A to B, composed of a rotation matrix $$R_B^A \in SO(3),$$

and a translation vector $$\vec{p}_B^A$$

$\in \mathbb{R}^3$. In the experimental embodiment, the global reference frame for the robotic implementation was chosen as the base frame of the robot, denoted by frame R. Let C and P represent the frames attached to the camera and tip of the ultrasound probe. Since in the experimental embodiment both camera and probe are rigidly affixed to the robot's end effector, $$T_R^C$$

and $$T_R^P$$

are constant.

$$T_R^C$$

is estimated by performing an eye-in-hand calibration, whereas $$T_R^P$$

is evaluated from the CAD model of the probe and its holder. Note that these transformations are composed of two transformations, namely:

$$T_R^C = T_R^{EE} T_{EE}^C \tag{4}$$

$$T_R^P = T_R^{EE} T_{EE}^P \tag{5}$$

In Equations (4) and (5), EE corresponds to the robot's end effector frame. The holder in the experimental embodiment was designed such that the frame of the ultrasound probe would be translated by a fixed distance along the z-direction of the manipulator's end effector frame. Thus in the physical workspace, the relationship used to map out the point cloud data (frame PC) to the robot's base frame can be expressed as, by way of non-limiting example:

$$T_R^{PC} = T_R^C T_C^{PC} \tag{6}$$

The anonymous CT patient scans (frame CT) were used to generate the mesh model (frame M) of the torsos, and hence the transformation between the two is known, set as $$R_{CT}^M = I, \text{ and } \vec{p}_{CT}^M = [0, 0, 0]^T.$$

The transformation $$T_{PC}^M$$

between the point cloud data and mesh model was estimated through the pointmatcher library using the iterative closest point approach. Initial target points were either defined in the CT scans, or on the mesh models, both of which correspond to the M frame. Since the ultrasound probe target position and orientation are defined in the ultrasound probe frame (P), the following transformation may be used:

$$T_P^M = T_R^{P-1} T_R^C T_C^{PC} T_{PC}^M \tag{7}$$

By way of non-limiting example, the overall control algorithm can be described through three major motion strategies: (a) positioning of the ultrasound probe near the target point, (b) tapping motion along the ribcage in the vicinity of the target point to collect displacement data at 20 N force, and (c) definition of an updated scanning position to avoid ribs, followed by a pre-defined sweeping motion along the probe's z-axis.

The trajectory generation of the manipulator in the experimental embodiment was performed by solving for the joint angles $\theta_i$, $i \in [0,5]$ through inverse kinematics computation facilitated by Open Robotics Control Software (OROCOS), and the built-in arm controller in the robot driver. Since obstacle avoidance has not been explicitly integrated into the robot's motion generator, the experimental embodiment defined a manipulator home configuration, from which the system can reach various target locations without colliding with the patient and table. The home configuration was centered at the patient's torso at an elevation of ~0.35 m from the body, with the +z-axis of the end effector corresponding to the −z-axis of the robot's base frame. The robot was driven to the home configuration before each target scan.

For the experimental embodiment, the force-displacement collection task began with the robot maintaining the probe's orientation fixed (as defined by the goal), and moving parallel to the torso at regular intervals of 3 mm, starting at 15 mm away from the goal point, and ending 15 mm past the goal point, resulting in a total of eleven readings. The robot thus moved along the end effector's+z-axis, registering the probe's position when a force reading is first recorded, and when a 20 N force is reached. The $L_2$ norm of the difference of these positions was stored as a displacement data point. The two data points that represent the smallest displacements were assumed to be rib landmarks, representing the center of the corresponding rib. The ideal direction of the applied force would be normal to the centerline of the curved section of the probe, however it may not always be the case as some regions in the lungs might only be reachable with the resultant force pushing the probe on the side. In the case where the measured lateral forces contributed to the overall force by over 20%, the overall force was then considered in the computations. The center of mass of the probe holder is not in line with the assumed center, however, it is stiff enough to prevent bending.

Since the goal point is located between two ribs, it can hence be localized with respect to the center of the two adjacent ribs. The goal point was thus projected onto the shortest straight segment separating the center of the ribs, that is also closest to the goal point itself. Let the distance of the goal point from Rib 1 be $d_l$. Because the ribs are fairly close to each other, a straight line connecting the two was assumed to avoid modeling the curvature of a torso. Once two points with the smallest displacement were identified from the force collection procedure, a line connecting the two was defined in the end effector's coordinate frame, and distance $d_1$ was computed along that line from Rib 1 to define the position of the updated target point. Maintaining the same orientation, the robot was thus driven to the updated goal point, the end effector then moved along the probe's+z-axis until a 20 N force is reached, followed by a sweeping motion of ±30° around the probe's line of contact with the patient.

VII. Experimental Results: Scanning Points Detection

To evaluate the effectiveness of the scanning point detection algorithm of the experimental embodiment, its results were compared to an expert radiologist's proposed scanning points on the surface of n=3 patients using CT data in 3D Slicer.

Figure 6:
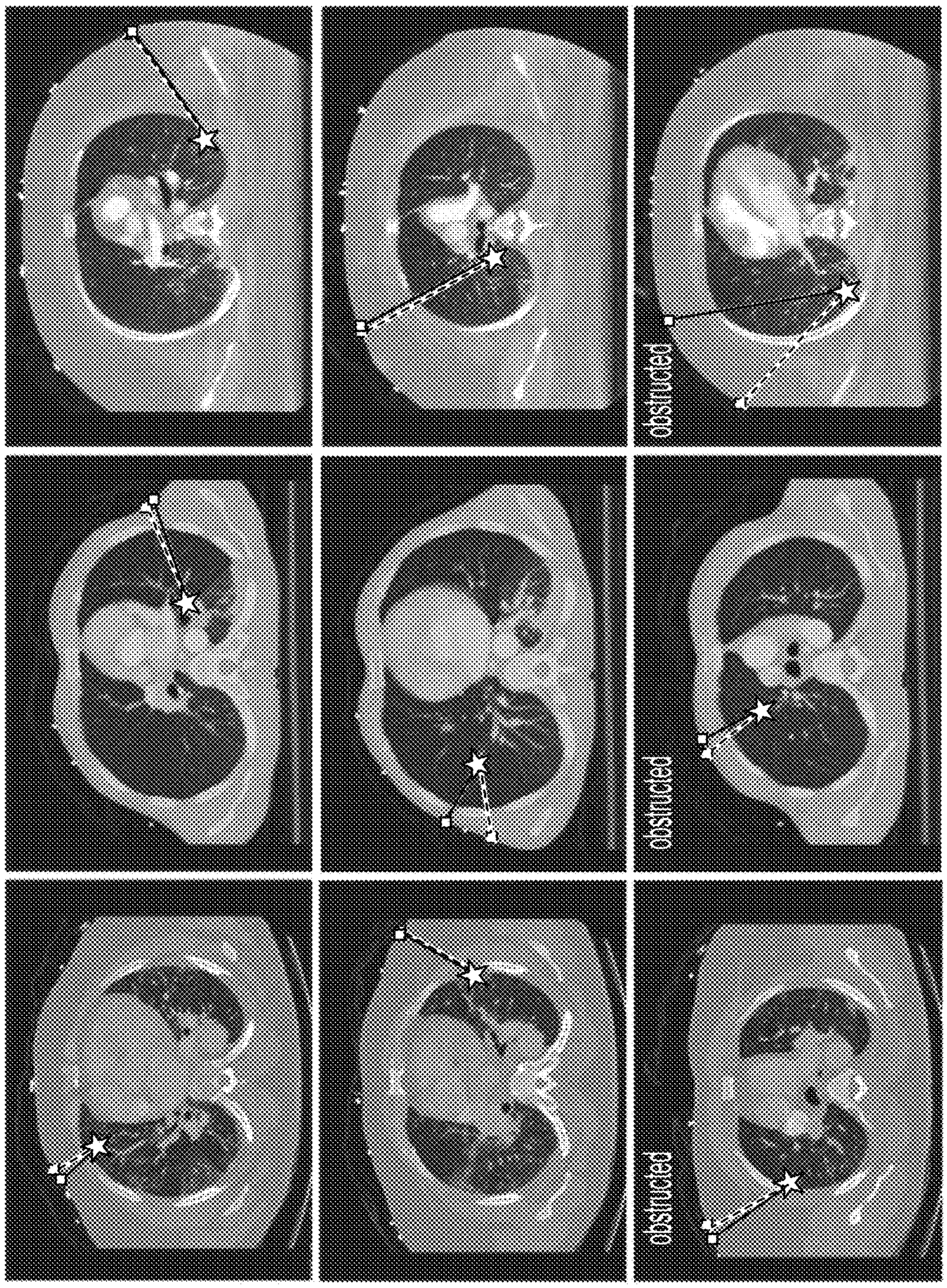
FIG. 6 depicts results of scanning obtained according to an experimental embodiment compared to results obtained according to a medical expert's selection.

FIG. 6 depicts results 600 of scanning obtained according to the experimental embodiment compared to results obtained according to a medical expert's selection. Scans 602 and 604 are of patients who were positive for COVID-19 and exhibited significant infiltrate formation in their lungs, whereas scans 606 are of a patient who was healthy with no lung abnormalities. The dashed lines mark the expert's proposed paths, and the solid lines are the ones proposed by the algorithm. The stars are the target points to be imaged in the lungs. Paths returned by the expert that were obstructed by ribs are marked as such.

The medical expert selected ten different targets within the lungs of each patient at various locations (amounting to a total of 30 data points) and proposed corresponding probe position and orientation on the CT scans that would allow them to image the selected targets through ultrasound. The medical expert only reviewed the CT slices along the main planes (sagittal, transverse and coronal).

The following metrics were used to compare the expert's selection to the algorithm's output: (a) bone obstruction, which is a qualitative metric that indicates whether the path of the ultrasound center beam to the goal point is obstructed by any skeletal structure, and (b) the quality of the ultrasound image, which was estimated using the overall weight structure described herein, whereby a smaller scan weight signals a better scan, with less air travels, scattering, reflection and refraction. For a fair initial comparison, the image search was restricted in the detection algorithm to the plane considered by the medical expert, i.e., the scanning point was evaluated across a single image that passes through the target point.

In this setting, the algorithm did not return solutions that were obstructed by bones, whereas five out of 30 of the medical expert's suggested scanning locations resulted in obstructed paths.

The quality of the scans have been compared on the remaining unobstructed 25 data points, and it was found that the algorithm returned paths with an overall 6.2% improvement in ultrasound image quality as compared to the expert's selection based on the returned sum of weights. However, when the algorithm was reset to search for optimal scanning locations across several tilted 2D images, the returned paths demonstrated a 14.3% improvement across the 25 data points, indicating that it can provide estimates superior to an expert's suggestion that was based on exclusively visual cues. The remaining five points have also been tested on the algorithm, and optimal scanning locations were successfully returned.

The average runtime for the detection of a single scanning position and orientation is 10.5±2.1 min, evaluated from the aforementioned 30 target points. The two most time consuming tasks are the generation of oblique planes from the CT scans, and the Gustafson-Kessel clustering used to delineate lung air. Since this is a pre-processing step, the rather large time consumption is not a concern.

VIII. Experimental Results: Ribcage Landmark Prediction

A total of 570 volumes were prepared from thorax CT scans, 550 of which were used for training, and 20 for testing. Each of the 570 volumes came from a different patient. In the training set, the minimum ribcage height was 195 mm, and maximum height 477 mm, whereas in the testing set, the minimum ribcage height was 276 mm, and maximum height 518 mm. The percentile distribution of the training and testing ribcage heights is detailed in Table 1.

TABLE 1

| | Percentile | | | | | | | | |
|---|---|---|---|---|---|---|---|---|---|
| Ribcage Height (mm) | $10^{th}$ | $20^{th}$ | $30^{th}$ | $40^{th}$ | $50^{th}$ | $60^{th}$ | $70^{th}$ | $80^{th}$ | $90^{th}$ |
| Training Set | 282 | 293 | 304 | 321 | 344 | 372 | 388 | 407 | 428 |
| Testing Set | 337 | 351 | 363 | 371 | 379 | 399 | 407 | 432 | 447 |

Figure 7:
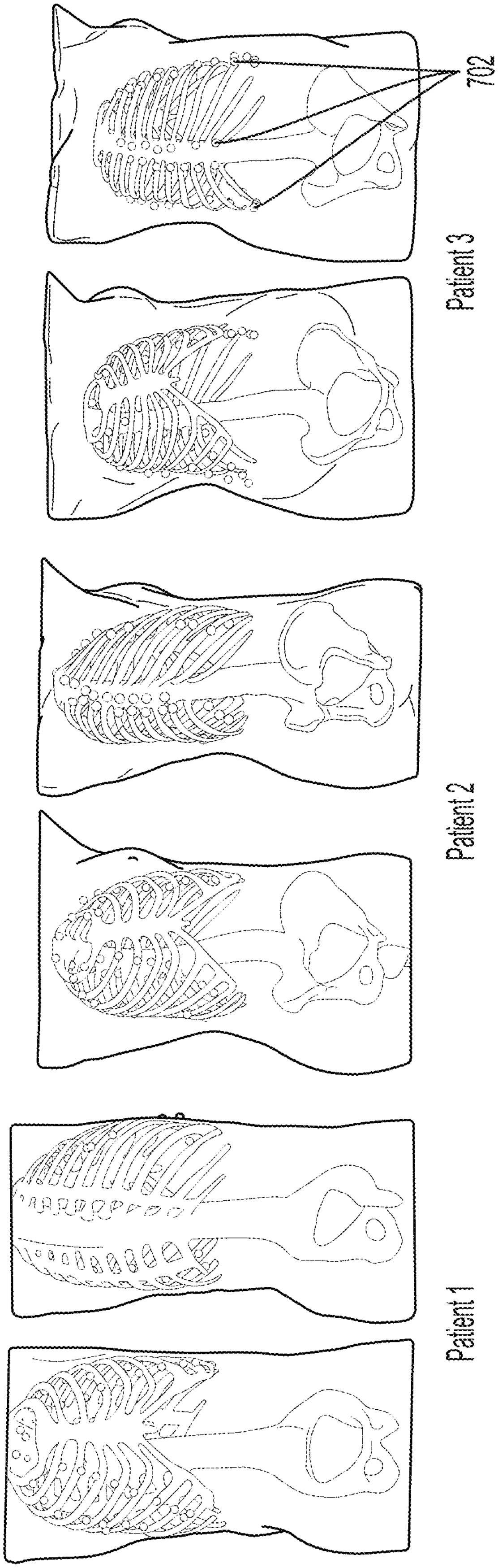
FIG. 7 depicts images of ribcage landmarks superimposed on skeletons according to various embodiments.
Figure 8:
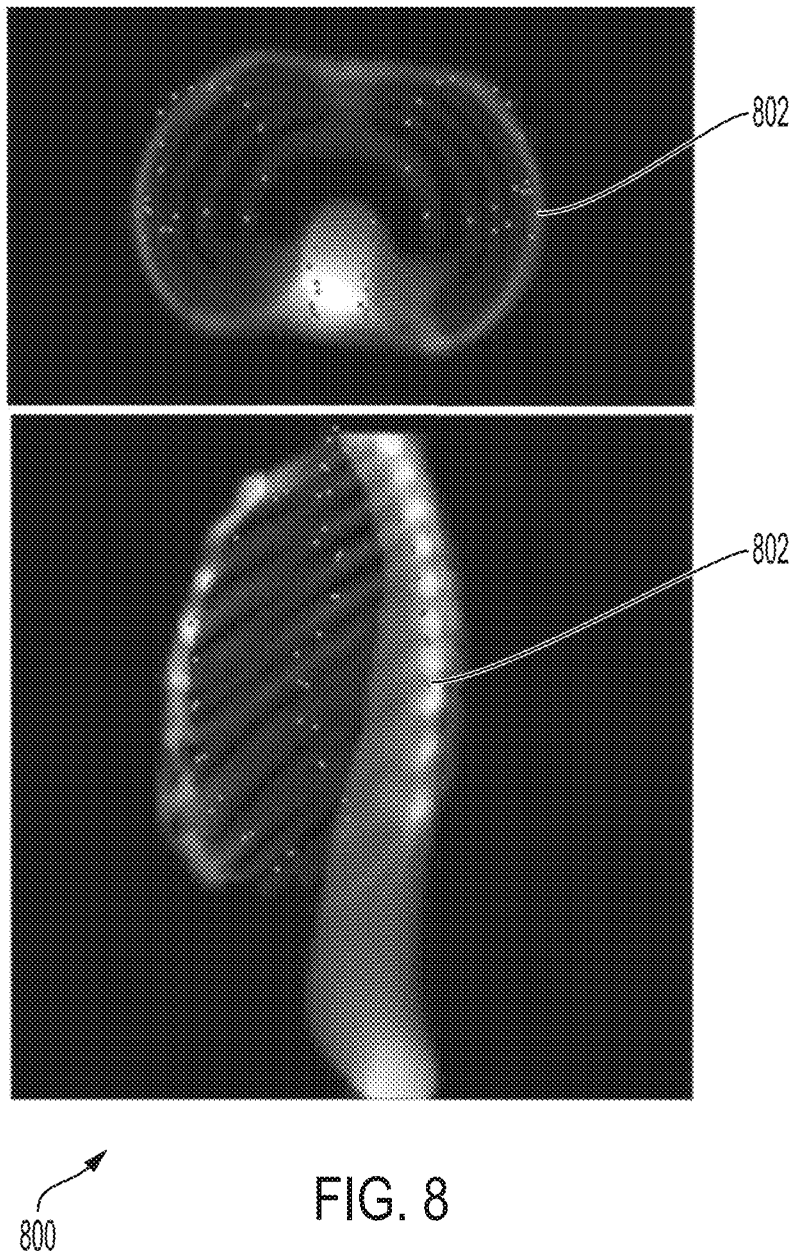
FIG. 8 depicts images of ribcage landmarks projected onto a patient according to various embodiments.

The network was trained for 150 epochs optimizing the $L_1$ distance between the predicted coordinates and the Ground truth coordinates using the Adam optimizer. The training took place on an NVIDIA Titan Xp GPU using the PyTorch framework, and converged in 75 min. A mean Euclidean error of 14.8±7 mm was observed on the unseen testing set, with a $95^{th}$ percentile of 28 mm. The overall inference time was on average 0.15 s. FIG. 7 shows the landmark predictions obtained using the trained model on the three human subjects discussed herein, by taking their corresponding skin surface masks as input. FIG. 8 shows the projected landmarks in 2D images.

FIG. 7 depicts images 700 of ribcage landmarks, e.g., landmarks 702, superimposed on skeletons according to various embodiments. In particular, FIG. 7 illustrates landmarks, e.g., landmarks 702, represented as dots output for the three patients and superimposed on the ribcages. The ribcage acts as ground truth for bone detection using the proposed landmarks. The skeletons were used for visualization purposes, and were not part of the training process.

FIG. 8 images 800 of ribcage landmarks, e.g., landmarks 802, projected onto a patient according to various embodiments. In particular, FIG. 8 depicts predicted landmarks, e.g., landmarks 802, on Patient 1 as seen through head-feet projection (top), as well as lateral projection (bottom). The landmarks are not part of the lungs, but merely appear so because of the projection.

IX: Experimental Results: Evaluation of Experimental Embodiment

A. Simulation Evaluation

A total of four experiment sets were devised to evaluate the experimental embodiment: (a) with prior CT scans without force feedback, (b) with prior CT scans with force feedback, (c) with ribcage landmark estimation without force feedback, and (d) with ribcage landmark estimation with force feedback. The overall performance of the robotic system was assessed in comparison to clinical requirements, which encompass three major elements: (a) prevention of acoustic shadowing effects whereby the infiltrates are blocked by the ribcage, (b) minimization of distance traveled by the ultrasound beam to reach targets, particularly through air, and (c) maintaining a contact force below 20 N between the patient's body and ultrasound probe.

Due to the technical limitations imposed by the spread of COVID-19 itself, the real-life implementation of the experimental embodiment was limited to n=1 phantom. Additional results are thus reported using Gazebo simulations. The same three patients described herein were used for the simulation. Since Gazebo is not integrated with an advanced physics engine for modeling tissue deformation on a human torso, the force sensing mechanism was replaced with a ROS node that compensated for the process of applying a force of 20 N and measuring the displacement of the probe through a tabular data lookup, obtained from the FEA simulations. In other words, when the ultrasound probe in the simulation approached the torso, instead of pushing through and measuring the displacement for a 20 N force (which is not implementable in Gazebo for such complex models), the end effector was fixed in place, and returned a displacement value which was obtained from prior FEA simulations on the corresponding torso model.

To replicate a realistic situation with uncertainties and inaccuracies, the torso models were placed in the simulated world at a pre-defined location, corrupted with noise in the x, y, and z directions, as well as roll, pitch, yaw angles. Errors were estimated based on reported camera accuracy, robot's rated precision, and variations between original torsos design and final model. The noises were sampled from Gaussian distributions with the pre-computed means, using a standard deviation of 1% of the mean. The numerical estimates on the errors are reported in Table 2. The exact location of the torsos was thus unknown to the robot. For each torso model, a total of eight points were defined for the robot to image, four on each side. Each lung was divided into four quadrants, and the eight target points correspond to the centroid of each quadrant (see FIG. 9). This approach was based on the eight-point POCUS of lungs. The exact location of the torso was used to assess the probe's position with respect to the torso, and provide predicted ultrasound scans using CT data.

TABLE 2

| | x | y | z | R | P | Y |
|---|---|---|---|---|---|---|
| registration | 5 | 5 | 30 | 0.10 | 0.10 | 0.10 |
| robot | 0.1 | 0.1 | 0.1 | 0.01 | 0.01 | 0.01 |
| model | 10 | 10 | 10 | 0.05 | 0.05 | 0.05 |
| total | ~15 | ~15 | ~40 | 0.16 | 0.16 | 0.16 |

Figure 9:
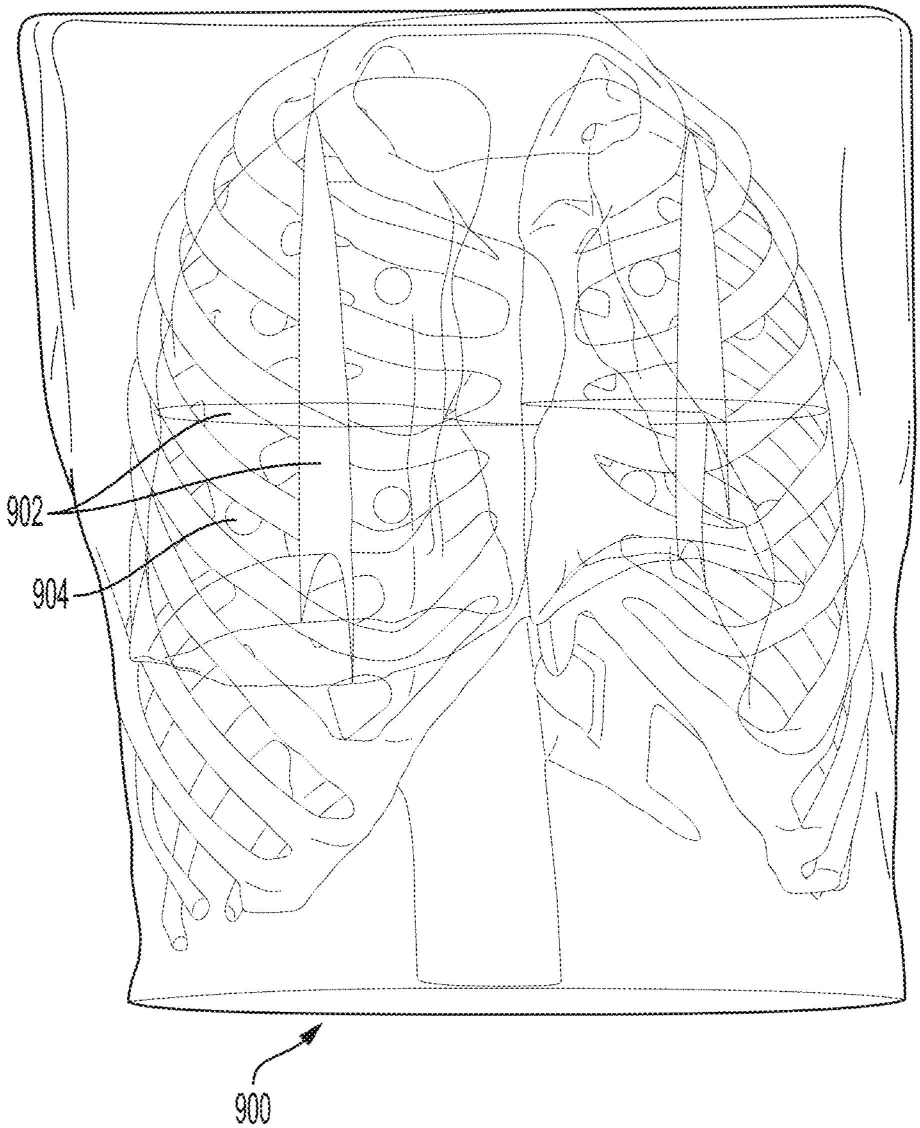
FIG. 9 depicts an image of lung regional centroids according to various embodiments.

FIG. 9 depicts an image 900 of lung regional centroids, e.g., centroids 904, according to various embodiments. Each lung was divided into four regions by partitions 902, the centroids of which, e.g., centroids 904, were computed and used as target points in the scanning point detection algorithm of the experimental embodiment.

Two main evaluation metrics were considered: (a) the positional accuracy of the final ultrasound probe placement, which is the $L_2$ norm of the difference between the target ultrasound position, and the actual final ultrasound position, and (b) a binary metric for imaging the goal infiltrate or region, whereby it is either visualized or obstructed. Each experiment set was repeated ten times with different sampled errors at every iteration. The results of all four experiment sets are reported in Table 3.

TABLE 3

| | Case 1 | Case 2 | Case 3 | Case 4 |
|---|---|---|---|---|
| Patient 1 | | | | |
| Average Error in x | 13.7 | 9.4 | 16.5 | 12.3 |
| Average Error in y | 12.7 | 10.1 | 14.6 | 6.70 |
| Average Error in z | 30.3 | 11.5 | 31.2 | 8.10 |
| Total Error | 35.5 | 17.9 | 38.1 | 16.1 |
| Standard Deviation | 18.2 | 12.8 | 18.5 | 16.8 |
| Patient 2 | | | | |
| Average Error in x | 14.2 | 13.2 | 12.4 | 11.2 |
| Average Error in y | 10.5 | 8.70 | 15.3 | 13.4 |
| Average Error in z | 41.0 | 13.5 | 35.6 | 15.1 |
| Total Error | 44.6 | 20.7 | 40.6 | 23.0 |
| Standard Deviation | 23.4 | 14.5 | 9.80 | 16.2 |
| Patient 3 | | | | |
| Average Error in x | 17.8 | 15.0 | 19.8 | 11.3 |
| Average Error in y | 13.6 | 13.9 | 12.4 | 10.9 |
| Average Error in z | 35.6 | 11.1 | 39.1 | 13.2 |
| Total Error | 42.0 | 23.2 | 45.5 | 20.5 |
| Standard Deviation | 18.7 | 16.7 | 21.4 | 17.6 |

In Table 3, Case 1 represents using CT data without force feedback; Case 2 represents using CT data with force feedback; Case 3 represents using landmark prediction only without force feedback; and Case 4 represents using landmark prediction only with force feedback. All values in Table 3 are in mm.

It is noticeable that the force feedback component has decreased the overall error on the probe's placement by 49.3% using prior CT scans, and 52.2% using predicted ribcage landmarks. The major error decrease was observed along the z-axis, since the force feedback ensured that the probe was in contact with the patient. It also provided additional information on the ribs' placement near the target points, which were used to define the same target points positions relative to the ribs' location as well. For the ultrasound probe placement using only force-displacement feedback, the average error across all three models was 20.6±14.7 mm. Using the final probe's placement and orientation on the torso, this data was converted into CT coordinates to verify that the point of interest initially specified was imaged. In all of the cases, the sweeping motion allowed the robot to successfully visualize all points of interest. When using ribcage landmark estimation, the displacement error with force feedback for all three patients averaged at 19.8±16.9 mm. Similarly, the data was transformed into CT coordinates, showing that all target points were also successfully swept by the probe. The average time required for completing an eight-point POCUS scan on a single patient was found to be 3.3±0.3 min and 18.6±11.2 min using prior CT scans with and without force feedback, respectively. The average time for completing the same scans was found to be 3.8±0.2 min and 20.3±13.5 min using predicted ribcage landmarks with and without force feedback, respectively. The reported durations do not include the timing to perform camera registration to the robot base, as it is assumed be known a priori.

B. Phantom Evaluation

The same eight points derived from the centroids of the lung quadrants were used as target points for the physical phantom. Since the manufactured phantom does not contain lungs or visual landmarks, the methodology was evaluated qualitatively, categorizing images into three major groups: (a) completely obstructed by bones, whereby 50-100% of the field of view is uninterpretable, with the goal point shadowed, (b) partially obstructed by bones, whereby <$50% of the field of view is uninterpretable, with the goal point not shadowed, and (c) unobstructed, whereby <10% of the field of view is uninterpretable, and the goal point not shadowed. Since the scanning point algorithm focuses on imaging a target point in the center of the ultrasound window, this metric is also reported for completeness. The phantom was assessed by an expert radiologist, confirming that the polycarbonate from which the ribcage is made is clearly discernible from the rest of the gelatin tissues. It does, however, allow for the ultrasound beam to traverse it, meaning that the "shadow" resulting from the phantom's rib obstruction will not be as opaque as that generated by human bones. The robot manipulator was first driven to the specified goal point, and displacement profiles were collected in the vicinity of the target. The ribs' location was estimated from the force-displacement profile, and the final goal point was recomputed as a distance percentage offset from one of the ribs. Each experiment set was repeated three times, the results of which are reported in Table 4. The evaluation of the ultrasound images was performed by an expert radiologist.

TABLE 4

| | Completely Obstructed | Partially Obstructed | Unobstructed | Visible Center |
|---|---|---|---|---|
| Case 1 | 6 | 3 | 15 | 18 |
| Case 2 | 0 | 4 | 20 | 24 |
| Case 3 | 10 | 1 | 13 | 14 |
| Case 4 | 3 | 3 | 16 | 19 |

In Table 4, Case 1 represents using CT data without force feedback; Case 2 represents using CT data with force feedback; Case 3 represents using landmark prediction only without force feedback; and Case 4 represents using landmark prediction only with force feedback.

Figure 10:
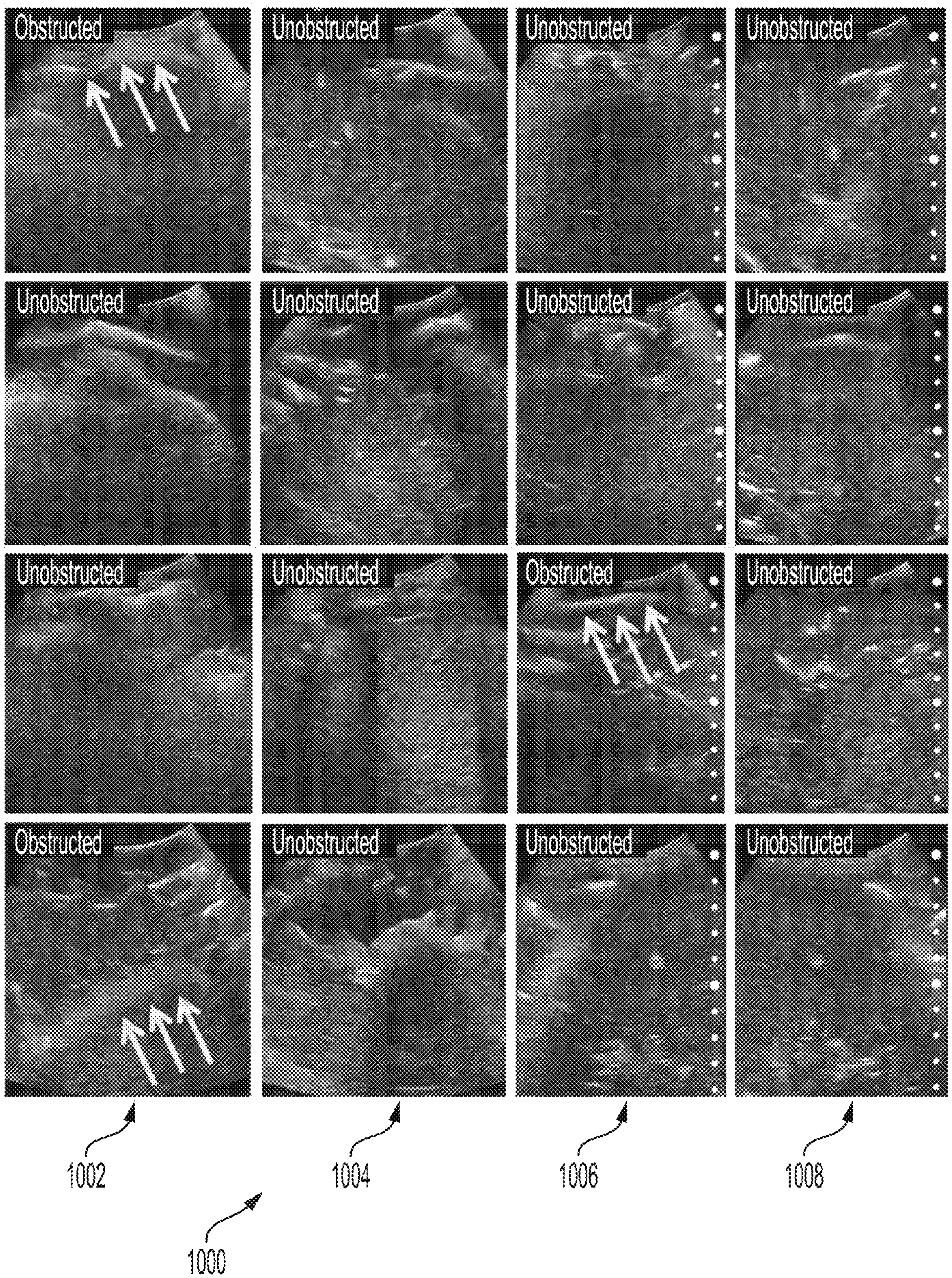
FIG. 10 depicts ultrasound scans of a phantom according to the experimental embodiment.

Results show that the force feedback indeed assisted with the avoidance of bone structures for imaging purposes, whereby 100% of the ultrasound scans using prior CT data were interpretable i.e., with a visible center, and 87.5% of the scans were interpretable using landmark estimation. Results without using force feedback show that 75% of scans have a visible center region using prior CT scans, and 58.3% using predicted landmarks. The landmark estimation approach demonstrated worse results due to errors associated with the prediction. Select images for all four experiments are shown in FIG. 10. The average time required for completing an eight-point POCUS scan on the phantom was found to be 3.4±0.0 min and 17.3±5.1 min using prior CT scans with and without force feedback, respectively. The average time for completing the scans was found to be 3.3±0.0 min and 25.8±7.4 min using predicted ribcage landmarks with and without force feedback, respectively. Camera registration time was not included in reported durations.

FIG. 10 depicts ultrasound scans 1000 of a phantom according to the experimental embodiment. Scans that are obstructed by bones are marked as such, with the arrows pointing towards the bone. Each column represents a different experiment, namely: scans using CT data without force feedback 1002; scans using CT data with force feedback 1004; scans using landmark prediction only without force feedback 1006; and scans using landmark prediction only with force feedback 1008.

X. Conclusion

Thus, this disclosure presents an autonomous—e.g., operational without human involvement—robotic ultrasound solution, e.g., for diagnosing and monitoring COVID-19 patients' lungs by imaging specified lung infiltrates. In the prior art, a sonographer initially palpates the patient's torso to assess the location of the ribs for correctly positioning the ultrasound probe. By contrast, some embodiments remove the need for proximity of a human technician and instead act autonomously. For example, some embodiments autonomously locate a position of a patient's ribcage relative to an ultrasound probe. Some embodiments autonomously produce an electronic three-dimensional patient-specific representation of a ribcage of a patient. Some embodiments autonomously provide an electronic representation of a target location, e.g., in or on the organ within the ribcage of the patient. According to some embodiments, a target location, e.g., in or on the organ within the ribcage of the patient, may be specified by a human, which may be the only human involvement in obtaining an ultrasound image of the target location. Some embodiments autonomously determine position and orientation of an ultrasound probe to acquire an image of a target location, e.g., in or on an organ within a ribcage of a patient. Some embodiments autonomously direct, by a robot, an ultrasound probe on a patient to acquire an image of a target location, e.g., in or on an organ within a ribcage of a patient. In some embodiments, no human technician needs to be proximate to the patient, e.g., in the same room as the patient or inside a bioprotective container with the patient, when the ultrasound scan is performed.

Both an autonomous robotic system that targets the monitoring of COVID-19 induced pulmonary diseases in patients and testing thereof is disclosed herein. An algorithm that can estimate the appropriate, e.g., optimal, position and orientation of an ultrasound probe on a patient's body to image target points in lungs identified using prior patient CT scans may be used. The algorithm makes use of the CT scan to assess the location of ribs, which should be avoided in ultrasound scans. In the case where CT data is not available, a deep learning algorithm that can predict 3D landmark positions of a ribcage given a torso surface model that can be obtained using a depth camera may be used. These landmarks are subsequently used to define target points on the patient's body. The target points, whether from prior CT scans or from deep learning applied to a torso surface model, are relayed to a robotic system. An optional force-displacement profile collection methodology allows the system to subsequently correct the ultrasound probe positioning on the phantom to avoid rib obstruction. An experimental embodiment was successfully tested in a simulated environment, as well as on a custom-made patient-specific phantom. Results have suggested that the force feedback enabled the robot to avoid skeletal obstruction, thus improving imaging outcomes, and that landmark estimation of the ribcage is a viable alternative to prior CT data.

Though described herein primarily relative to a patient's lung, where the bony obstruction is the patient's ribcage, embodiments are not so limited. For example, embodiments may be used to acquire an ultrasound image of any location in or on any organ entirely or partially present within a patient's ribcage, e.g., a lung, a heart, a spleen, a liver, a pancreas, or a kidney. As another example, embodiments may be used to acquire an ultrasound image of any location in or on any organ entirely or partially present within a patient's pelvic and/or hip bones, e.g., a urinary bladder, a rectum, a sigmoid colon, a urethra, a uterus, a fallopian tube, an ovary, a seminal vesicle, or a prostate gland.

Certain embodiments can be performed using a computer program or set of programs executed by an electronic processor. The computer programs can exist in a variety of forms both active and inactive. For example, the computer programs can exist as software program(s) comprised of program instructions in source code, object code, executable code or other formats; firmware program(s), or hardware description language (HDL) files. Any of the above can be embodied on a transitory or non-transitory computer readable medium, which include storage devices and signals, in compressed or uncompressed form. Exemplary computer readable storage devices include conventional computer system RAM (random access memory), ROM (read-only memory), EPROM (erasable, programmable ROM), EEPROM (electrically erasable, programmable ROM), and magnetic or optical disks or tapes.

While the invention has been described with reference to the exemplary embodiments thereof, those skilled in the art will be able to make various modifications to the described embodiments without departing from the true spirit and scope. The terms and descriptions used herein are set forth by way of illustration only and are not meant as limitations. In particular, although the method has been described by examples, the steps of the method can be performed in a different order than illustrated or simultaneously. Those skilled in the art will recognize that these and other variations are possible within the spirit and scope as defined in the following claims and their equivalents.

What is claimed is:

1. A method of autonomously robotically acquiring an ultrasound image of an organ within a bony obstruction of a patient, the method comprising:

acquiring an electronic three-dimensional patient-specific representation of the bony obstruction of the patient;

obtaining an electronic representation of a target imaging location in or on the organ within the bony obstruction of the patient;

determining, automatically, a position and orientation of an ultrasound probe to acquire an image of the target imaging location, wherein the determining comprises determining the position and orientation based on a weighted function of a plurality of material densities, wherein the weighted function comprises a non-zero weight for bone material, a non-zero weight for air material, and a non-zero weight for soft tissue material, and wherein the weighted function comprises weights for pixels of the electronic three-dimensional patient-specific representation in between a point of contact of the ultrasound probe and the target imaging location; and directing, autonomously, and by a robot, the ultrasound probe on the patient to acquire the image of the target imaging location based on the position and orientation.

2. The method of claim 1, further comprising outputting the image of the target imaging location.

3. The method of claim 1, wherein the bony obstruction comprises a ribcage, and wherein the organ comprises at least one of: a lung, a heart, a spleen, a liver, a pancreas, or a kidney.

4. The method of claim 1, wherein the acquiring comprises acquiring a three-dimensional radiological scan of the patient.

5. The method of claim 1, wherein the acquiring comprises acquiring a machine learning representation of the bony obstruction of the patient based on a topographical image of the patient.

6. The method of claim 1, wherein the obtaining comprises obtaining a human specified location in the electronic three-dimensional representation of the bony obstruction of the patient.

7. The method of claim 1, further comprising:

measuring a force on the ultrasound probe; and determining a position of the ultrasound probe, based on the force, relative to the bony obstruction of the patient.

8. The method of claim 1, wherein the plurality of material densities comprises a bone density.

9. The method of claim 8, wherein the organ comprises a lung, and wherein the plurality of material densities further comprises a density of air.

10. The method of claim 1, wherein an image of the target imaging location is acquired without requiring proximity of a technician to the patient.

11. A system for autonomously robotically acquiring an ultrasound image of an organ within a bony obstruction of a patient, the system comprising:

an electronic processor that executes instructions to perform operations comprising:

acquiring an electronic three-dimensional patient-specific representation of the bony obstruction of the patient, obtaining an electronic representation of a target imaging location in or on the organ within the bony obstruction of the patient, and determining, automatically, a position and orientation of an ultrasound probe to acquire an image of the target imaging location, wherein the determining comprises determining the position and orientation based on a weighted function of a plurality of material densities, wherein the weighted function comprises a non-zero weight for bone material, a non-zero weight for air material, and a non-zero weight for soft tissue material, and wherein the weighted function comprises weights for pixels of the electronic three-dimensional patient-specific representation in between a point of contact of the ultrasound probe and the target imaging location; and a robot communicatively coupled to the electronic processor, the robot comprising an effector couplable to an ultrasound probe, the robot configured to direct the ultrasound probe on the patient to acquire the image of the target imaging location based on the position and orientation.

12. The system of claim 11, wherein the operations further comprise outputting the image of the target imaging location.

13. The system of claim 11, wherein the bony obstruction comprises a ribcage, and wherein the organ comprises at least one of: a lung, a heart, a spleen, a liver, a pancreas, or a kidney.

14. The system of claim 11, wherein the acquiring comprises acquiring a three-dimensional radiological scan of the patient.

15. The system of claim 11, wherein the acquiring comprises acquiring a machine learning representation of the bony obstruction of the patient based on a topographical image of the patient.

16. The system of claim 11, wherein the obtaining comprises obtaining a human specified location in the electronic three-dimensional representation of the bony obstruction of the patient.

17. The system of claim 11, wherein the operations further comprise:

measuring a force on the ultrasound probe; and determining a position of the ultrasound probe, based on the force, relative to the bony obstruction of the patient.

18. The system of claim 11, wherein the plurality of material densities comprises a bone density.

19. The system of claim 18, wherein the organ comprises a lung, and wherein the plurality of material densities further comprises a density of air.

20. The system of claim 11, wherein the robot is configured to acquire an image of the target imaging location without requiring proximity of a technician to the patient.

* * * * *